United States Patent [19]

Sandhu et al.

[11] 4,452,008

[45] Jun. 5, 1984

[54] SEED COATINGS

[75] Inventors: Mohammad A. Sandhu; Clarence C. Dannelly; Bernard W. Oliver, Jr., all of Kingsport, Tenn.

[73] Assignee: Eastman Kodak Company, Rochester, N.Y.

[21] Appl. No.: 511,361

[22] Filed: Jul. 6, 1983

Related U.S. Application Data

[62] Division of Ser. No. 241,300, Mar. 6, 1981.

[51] Int. Cl.$^3$ ................................................. A01C 1/06
[52] U.S. Cl. .................................... 47/57.6; 71/64.07; 525/371
[58] Field of Search .......................... 47/57.6; 118/303; 427/4, 212; 71/77, 903, 64.07, 64.12; 525/371

[56] References Cited

U.S. PATENT DOCUMENTS 4,123,396 10/1978 Rembaum et al. .................. 525/371
4,126,438 11/1978 Pulli et al. ............................ 71/903
4,368,591 1/1983 Barke et al. .......................... 47/57.6

Primary Examiner—Robert E. Bagwill
Assistant Examiner—Bradley M. Lewis
Attorney, Agent, or Firm—John F. Stevens; Daniel B. Reece, III

[57] ABSTRACT

Disclosed are coating compositions comprising (a) the reaction product of a compound of titanium and a nitrogen-containing polymer, (b) an inert particulate filler material and (c) a water-permeable polymeric binder. These compositions are especially useful as coatings for leguminous seeds.

5 Claims, No Drawings

SEED COATINGS

This is a division of application Ser. No. 241,300 filed Mar. 6, 1981.

TECHNICAL FIELD

This invention relates to seed coating compositions comprising a complex of titanium and a polymer which are effective in improving the crop yield of legumes.

BACKGROUND

Titanium is neither considered essential to the growth of nor toxic to higher plants. It is insoluble in the pH range of 4–8 where plants normally grow in soil. It has been reported that potassium titanate added to solution cultures improved the growth of alfalfa. It also has been reported that titanium sulfate and potassium titanate increased the number and caused earlier formation of nodules. Titanium oxide is also believed to act as a photocatalyst in the photochemical oxidation of nitrite to nitrate. It has been reported that titanium enhances root growth. It is not believed, however, that titanium has been complexed with certain polymers to render it available to the growing plant when coated on the seed.

DISCLOSURE OF THE INVENTION

In accordance with the present invention, complexes of titanium and a polymer are used to improve crop yields of legumes such as soybeans. The complex is preferably coated onto the seeds prior to planting them. Complexes containing $Ti^{+4}$ are the especially preferred form of complex for this use. The improved results obtained by using the complex are surprising, since use of a typical titanium salt such as titanium citrate without the polymer, or use of the polymer without the titanium salt did not show improved results.

To maintain the titanium in the $Ti^{+4}$ state, it is reacted with a polymer having nitrogen available to complex with the titanium. Examples of suitable polymers include polyvinylpyridines such as polymers of 2-methyl-5-vinylpyridine and 4-methyl-5-vinylpyridine, vinyl amines, N-alkylamino, alkyl acrylates, and copolymers containing about 20–80% monomers with amino or pyridine moieties. The titanium and nitrogen-containing polymer are mixed with a suitable binder prior to application to the seeds. The binder should be water-soluble or at least water-permeable to allow water from the soil to contact the seed. Suitable binders include polymers such as polymers of acrylates, methacrylate, cellulose, styrene, etc. The titanium-containing coating dope is then applied to the seeds by methods well known in the art, a preferred method of which is described in U.S. Pat. No. 4,117,801, the specification of which is incorporated herein by reference. Water insoluble polymers can be made water permeable by the inclusion in the coating of an inert particulate material such as talc, graphite, etc.

A titanium salt is preferably reacted with a peroxide to form an oxygen-containing compound prior to reacting with the nitrogen-containing polymer. It is well known that oxygen aids in the germination of seeds.

In a preferred form of the invention, an aqueous solution of a salt of titanium such as titanium sulfate, citrate, isopropylate, chloride, bromide or oxalate is reacted at room temperature with a compound having available oxygen such as hydrogen peroxide. Typically, one mole of the titanium salt is reacted with about 1.1 mole of the peroxide. The resulting titanium compound, $TiO_2^{+2}$, is then reacted with a nitrogen-containing polymer such as polyvinylpyridine to form a titanium-oxygen-polymeric precipitate. This precipitate is dissolved or dispersed in a solvent with a binder and is then ready for use with the selected seeds.

While the ratio of the inert particulate material, the titanium-polymer complex and the binder may vary over a wide range, it is preferred that this ratio be from about 3:0.1:1 to about 1.5:0.5:1. It is preferred that the coating weight be from about 0.3 to about 5%, based on the weight of the seeds. Furthermore, it is preferred that the weight of titanium be from about 0.01 to about 0.2 grams per 100 grams seeds.

If desired, other additives such as growth promoters, fertilizers, fungicides, herbicides, etc., may be added to the coating composition prior to coating the seeds.

The invention will be further illustrated by the following examples although it will be understood that these examples are included merely for purposes of illustration and are not intended to limit the scope of the invention.

EXAMPLES

To a solution of titanium sulfate (160.0 g, 1.0 mole) in water (1500 ml) aqueous hydrogen peroxide (30%, 125 ml, 1.1 mole) is added with gentle stirring and a yellow-orange solution was obtained. The reaction mixture is evaporated to a thick slurry and was then diluted with methanol (200 ml). A solution of poly(2-methyl-5-vinylpyridine) (29.7 g, 0.25 mole) in methanol (200 ml) is added to the stirred reaction mixture. An orange precipitate is filtered and dried to give a yellow powder (125 g) of titanium $(Ti^{+4})$-polymer complex.

9.2 g Talc, 2.3 g polymer-titanium complex and 1.98 g poly(methyl methacrylate) in acetone are mixed giving a total volume of 200 ml. The solution is filtered through 60 mesh screen just prior to coating.

Two-hundred-fifty grams of soybean seeds are placed in the coating chamber of a conventional air-suspension coater. The blower is turned on to begin the air flow at 22 psi and the pump is turned on to initiate the application of the coating material. The air inlet temperature is 50°–60° C. and the air outlet temperature is 30°–32° C. As the air flow fluidizes the seeds within the coating chamber, the coating dope is contacted with the seeds. As the coating dope and the seed rise in the chamber, the solvent is evaporated. The partially coated seeds are recycled back to the coating chamber and were continuously coated for 15 minutes. The seeds are found to have coatings of a weight of about 4.3%, based on the weight of the seeds. The seeds are planted in a conventional manner in the same field, and given the same care such as fertilizers, insecticides, herbicides, etc. and at harvest the results are found as illustrated in Examples 1–15.

| Ex. | $Ti^{4+}$-Polymer g/100 g Seeds | $Ti^{+4}$ g/100 g Seeds | Seed Yield Normalized At 13% Moisture | |
|---|---|---|---|---|
| | | | g/20 Ft-Row | Bushels/Acre |
| 1 | Uncoated Seeds | | 1202 | 38.3 |
| 2 | 0.175 | 0.023 | 930 | 29.7 |
| 3 | 0.60 | 0.079 | 1570 | 50.1 |
| 4 | 1.7 | 0.224 | 1382 | 44.1 |
| 5 | Uncoated Seeds | | 1033 | 27.5 |
| 6 | 0 | 0 | 1015 | 27.0 |

-continued

| Ex. | $Ti^{4+}$-Polymer g/100 g Seeds | $Ti^{+4}$ g/100 g Seeds | Seed Yield Normalized At 13% Moisture | |
|---|---|---|---|---|
| | | | g/20 Ft-Row | Bushels/Acre |
| 7 | 0.18 | 0.024 | 999 | 26.6 |
| 8 | 0.37 | 0.049 | 1005 | 26.7 |
| 9 | 0.55 | 0.073 | 1096 | 29.1 |
| 10 | 0.73 | 0.096 | 1236 | 32.9 |
| 11 | Uncoated Seeds | | 2094 | 55.7 |
| 12 | 0.35 | 0.046 | 2094 | 55.7 |
| 13 | 0.69 | 0.091 | 2162 | 57.5 |
| 14 | 1.38 | 0.182 | 2201 | 58.5 |
| 15 | 0.73 | 0.096 | 2286 | 60.8 |

Unless otherwise specified, all parts, percentages, ratios, etc. are by weight.

The invention has been described in detail with particular reference to preferred embodiments thereof, but it will be understood that modifications and variations can be effected within the spirit and scope of the invention.

I claim:
1. Seeds of leguminous plants having a coating comprising the reaction product of a compound of titanium and a nitrogen-containing polymer.
2. Seeds of leguminous plants having a substantially continuous coating comprising the reaction product of a titanium compound and a polymer of 2-methyl-5-vinyl-pyridine.
3. Seeds according to claim 2 wherein said coating comprises a water-permeable binder.
4. Seeds according to claim 2 wherein said coating comprises an inert particulate filler material and a water-permeable binder.
5. Seeds of leguminous plants having a coating comprising
   (a) the reaction product of titanium and a nitrogen-containing polymer,
   (b) an inert particulate filler material and
   (c) a water-permeable polymeric binder, the ratio by weight of a:b:c being from about 0.1:3.0:1 to about 0.5:1.5:1.

* * * * *